United States Patent [19]

Schwan

[11] 3,971,788

[45] July 27, 1976

[54] 2-METHYL-3-PHENYL-1,2,3,10b-TETRAHYDRONINDENO[1,2,3-ij]-ISOQUINOLINE HYDROBROMIDE

[75] Inventor: Thomas J. Schwan, Norwich, N.Y.

[73] Assignee: Morton-Norwich Products, Inc., Norwich, N.Y.

[22] Filed: Mar. 7, 1975

[21] Appl. No.: 556,478

[52] U.S. Cl.............. 260/286 R; 260/570.6; 424/258
[51] Int. Cl.² ................................. C07D 217/02
[58] Field of Search ..................... 260/286 R

[56] References Cited
OTHER PUBLICATIONS

Campbell et al., J. Chem. Soc., (1958) pp. 4743–4746.
Schwan, J. Heterocycl. Chem. (1971) vol. 8(5), p. 839.

Primary Examiner—Paul M. Coughlan, Jr.
Attorney, Agent, or Firm—Anthony J. Franze

[57] ABSTRACT

A compound 2-methyl-3-phenyl-1,2,3,10b-tetrahydroindeno [1,2,3-ij]-isoquinoline hydrobromide of the formula:

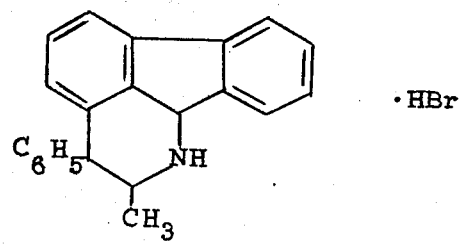

possesses pharmacological activity as an antidepressant.

1 Claim, No Drawings

2-METHYL-3-PHENYL-1,2,3,10b-TETRAHYDROINDENO[1,2,3-ij]-ISOQUINOLINE HYDROBROMIDE

This invention relates to a chemical compound. In particular it is concerned with a compound of the formula:

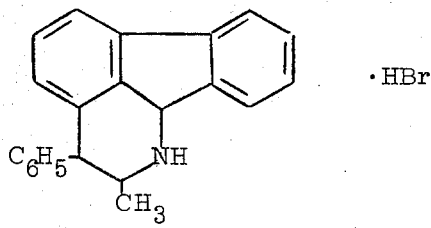

This compound possesses pharmacological activity affecting the central nervous system. When administered perorally to animals it exhibits antidepressant action. Its antidepressant property is evidenced in the control of tetrabenazine-induced ptosis in mice. An oral dose of 50 mg/kg of this compound to mice intraperitoneally receiving 35 mg/kg of tetrabenazine counteracts the ptosis producing property of tetrabenazine.

In order that this invention be readily available to and understood by those skilled in the art the following illustration is included:

A. 2-(9-Fluorenylamino)-1-phenylpropanol Hydrochloride

2-Amino-1-phenylpropanol 30.2 g (0.20 mole), 9-fluoroenone 36.0 g (0.20 mole), 0.4 g (0.0021 mole) of p-toluenesulfonic acid and 150 ml of toluene were placed in a 0.5 l. 3-necked flask and heated with stirring to reflux. The reaction mixture was refluxed for 31 hours until the theoretical amount of $H_2O$ was collected via a Dean-Stark trap. The reaction mixture was filtered and concentrated to dryness under reduced pressure to give 57 g (91%) of the crude product, a yellow-orange viscous oil.

A 57 g (0.18 mole) portion of the crude 2-(9-fluorenylideneamino)-1-phenylpropanol was taken up in 400 ml of methanol and was treated with 6.6 g (0.17 mole) of sodium borohydride at 5°–15° over 0.3 hours. The reaction mixture was stored overnight at room temperature and concentrated under reduced pressure to give a viscous residue which was hydrolyzed with 500 ml of $H_2O$ and extracted with 500 ml of chloroform. The chloroform extract was washed with 200 ml of water, dried over $MgSO_4$ and filtered. The filtrate was concentrated under reduced pressure to give 57 g (100%) of the free base as a light yellow-brown oil.

A 20 g portion of the free base was taken up in 400 ml of ether and treated with 13 ml of ethanolic HCl. The ether was decanted and the brown residue was dissolved in 700 ml of isopropanol and filtered. The filtrate was concentrated to one-seventh volume, refrigerated and filtered. The cream colored solid was washed with 50 ml of isopropanol, ether, air dried and dried to a constant weight at 60°, m.p. 251°–253° dec. Yield: 4.3 g (17%).

The analytical sample, m.p. 249°–251° dec.; was a portion of the above material dried for 24 hours at 100° in vacuo.

Anal. Calcd. for $C_{22}H_{21}NO.HCl$: C, 75.09; H, 6.30; N, 3.98. Found: C, 74.90; H, 6.30; N, 3.72.

B. 2-Methyl-3-phenyl-1,2,3,10b-tetrahydroindeno[1,2,3-ij]isoquinoline hydrobromide A 37.5 g (0.119 mole) portion of A (free base) in 150 ml of 48% HBr was refluxed for 20 hours with rapid stirring. The reaction mixture was cooled and the HBr decanted. The black residue was washed repeatedly with a total of 350 ml of ethyl acetate and filtered to give 5.2 g (12%) of a cream colored solid which was air dried, m.p. 297°–300° dec.

The decantate was cooled and filtered. The cream colored solid was washed with 80 ml of ethyl acetate and air dried, m.p. 293°–297° dec. Yield: 1.1 g (2%).

The analytical sample, m.p. 300°–303° dec., was recrystallized from methanol.

Anal. Calcd. for $C_{22}H_{19}N.HBr$: C, 69.84; H, 5.33; N, 3.70. Found: C, 69.83; H, 5.29; N, 3.51.

What is claimed is:

1. A compound of the formula:

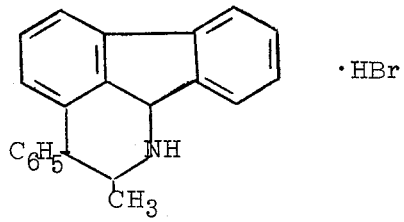

* * * * *